United States Patent
Melker et al.

(10) Patent No.: US 6,974,706 B1
(45) Date of Patent: Dec. 13, 2005

(54) APPLICATION OF BIOSENSORS FOR DIAGNOSIS AND TREATMENT OF DISEASE

(75) Inventors: Richard J. Melker, Gainesville, FL (US); Donn Michael Dennis, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/345,532

(22) Filed: Jan. 16, 2003

(51) Int. Cl.[7] ............................................. G01N 33/543
(52) U.S. Cl. ............................ 436/518; 422/84; 435/6; 435/7.1; 435/7.9; 435/7.92; 436/164; 436/172; 436/524; 436/528; 436/805; 436/811; 436/815; 436/900
(58) Field of Search ................................ 436/164, 172, 436/518, 524, 528, 805, 811, 815, 900; 435/4, 435/7.1, 7.9, 7.92, 6; 422/83, 84, 85, 86

(56) References Cited

U.S. PATENT DOCUMENTS

| | | |
|---|---|---|
| 4,334,540 A | 6/1982 | Preti et al. |
| 4,349,626 A | 9/1982 | Labows et al. |
| 4,534,360 A | 8/1985 | Williams |
| 4,772,559 A | 9/1988 | Preti et al. |
| 5,482,601 A | 1/1996 | Ohshima et al. |
| 5,645,072 A | 7/1997 | Thrall et al. |
| 5,861,254 A | 1/1999 | Schneider et al. |
| 5,996,586 A | 12/1999 | Phillips |
| 6,057,162 A | 5/2000 | Rounbehler et al. |
| 6,063,243 A | 5/2000 | Zettl et al. |
| 6,190,858 B1 | 2/2001 | Persaud et al. |
| 6,203,814 B1 | 3/2001 | Fisher et al. |
| 6,221,026 B1 | 4/2001 | Phillips |
| 6,248,078 B1 | 6/2001 | Risby et al. |
| 6,261,783 B1 | 7/2001 | Jayasena et al. |
| 6,303,316 B1 | 10/2001 | Kiel et al. |
| 6,312,390 B1 | 11/2001 | Phillips |
| 6,363,772 B1 | 4/2002 | Berry |
| 6,387,329 B1 | 5/2002 | Lewis et al. |
| 6,399,302 B1 | 6/2002 | Lannigan et al. |
| 6,479,019 B1 | 11/2002 | Goldstein et al. |
| 6,558,626 B1 * | 5/2003 | Aker et al. .................... 422/91 |
| 6,680,377 B1 | 1/2004 | Stanton et al. |
| 6,727,075 B2 * | 4/2004 | Fitzgerald et al. ............ 435/25 |
| 2001/0046674 A1 | 11/2001 | Ellington |
| 2002/0007249 A1 | 1/2002 | Cranley et al. |
| 2002/0034757 A1 | 3/2002 | Cubicciotti |
| 2002/0068295 A1 | 6/2002 | Madou et al. |
| 2002/0177232 A1 * | 11/2002 | Melker et al. ............... 436/151 |
| 2003/0004426 A1 * | 1/2003 | Melker et al. ............... 600/532 |
| 2003/0087239 A1 * | 5/2003 | Stanton et al. ................... 435/6 |
| 2004/0101477 A1 * | 5/2004 | Leyland-Jones ............ 424/9.2 |

FOREIGN PATENT DOCUMENTS

| | | |
|---|---|---|
| WO | WO 98/57145 | 12/1998 |

OTHER PUBLICATIONS

Brody et al., "The Use of Aptamers in Large Arrays for Molecular Diagnostics", *Molecular Diagnosis* (1999), 4(4): 381-388.

Liebich and Wöll, "Volatile Substances in Blood Serum: profile Analysis and Quantitative Determination", *Journal of Chromatography* (1977), 142: 505-516.

Paviou and Turner, "Sniffing out the Truth: Clinical Diagnosis Using the Electronic Nose", *Clin. Chem. Lab. Med.* (2000), 38(2): 99-112.

Brody and Gold, "Aptamers as Therapeutic and Diagnostic Agents", *Reviews in Molecular Biotechnology* (2000), 74: 5-13.

Stojanovic et al., "Aptamer-Based Folding Fluorescent Sensor for Cocaine", *J. Am. Chem. Soc.* (2001), 123: 4928-4931.

Fischer et al., "A Man-Portable Chemical Sniffer Utilizing Novel Fluorescent Polymers for Detection of Ultra-Trace Concentrations of Explosives Emanating from Landmines", *Nomadics Inc.* (2000), 1-10.

Rogers et al., "Fiber-Optic Biosensors Based on Total Internal-Reflection Fluorescence", *American Chemical Society* (1992), Ch. 13: 165-173.

* cited by examiner

*Primary Examiner*—Christopher L. Chin
(74) *Attorney, Agent, or Firm*—Saliwanchik, Lloyd & Saliwanchik

(57) ABSTRACT

A method for detecting compounds of interest in bodily fluids, including exhaled breath and blood. The present invention uses biosensors that mimic naturally occurring cellular mechanisms, including RNA oligonucleotide chains or "aptamers," in combination with molecular beacons or nanotechnology to provide an effective and efficient method for diagnosing a condition and/or disease within a patient. The subject invention also provides a method for screening those analytes/biomarkers likely to be present in exhaled breath.

2 Claims, No Drawings

APPLICATION OF BIOSENSORS FOR DIAGNOSIS AND TREATMENT OF DISEASE

GOVERNMENT SUPPORT

The subject matter of this application has been supported by a research grant from the National Science Foundation (Grant Number NSF: EEC 02-10580). Accordingly, the government may have certain rights in this invention.

BACKGROUND OF INVENTION

There is a great need for the development of efficient and accurate methods related to the detection and identification of chemical and biological agents (hereinafter "analyte") including, but not limited to, nucleic acids, proteins, illicit drugs, explosives, toxins, pharmaceuticals, carcinogens, poisons, allergens, and infectious agents. Current methods of detecting analytes require extraction of a sample into organic solvents, followed by analysis using stand alone analytical systems such as gas-liquid chromatography and/or mass spectroscopy. These methods are time-consuming and often expensive. The development of a biosensor device that could accurately and efficiently detect/screen for chemical and biological agents would therefore provide a significant cost and time benefit.

Three recent advancements in medicine are particularly germane to expanding the potential of detecting analytes, in particular with regard to the diagnosis and treatment of disease: nanotechnology, biodetectors (biosensors), and the identification of biomarkers for specific diseases and/or conditions. Nanotechnology, in particular nanoparticles, offers many advantages when used for applications such as the delivery of bioactive agents (i.e., DNA, AIDS drugs, gene therapy, immunosuppressants, chemotherapeutics), and drug uptake and degradation (i.e., enzyme encapsulation). For example, nanoparticles have been proposed as providing site-specific distribution of drugs to, and minimization of loss from, a target site. Appropriately sized particles have been proposed wherein such particles can be delivered to selected tissues to release their drug load in a controlled and sustained manner.

The term "biodetectors" or "biosensors" relates to the use of naturally occurring and synthetic compounds as highly specific and extraordinarily sensitive detectors of various types of molecules and markers of disease. Biosensor manufacture mimics the naturally occurring mechanisms of DNA, RNA, and protein synthesis in cells.

Aptamers have recently been identified as potentially effective biosensors for molecules and compounds of scientific and commercial interest (see Brody, E. N. and L. Gold, "Aptamers as therapeutic and diagnostic agents," *J. Biotechnol.*, 74(1):5–13 (2000) and Brody et al., "The use of aptamers in large arrays for molecular diagnostics," *Mol. Diagn.*, 4(4):381–8 (1999)). For example, aptamers have demonstrated greater specificity and robustness than antibody-based diagnostic technologies. In contrast to antibodies, whose identification and production completely rest on animals and/or cultured cells, both the identification and production of aptamers takes place in vitro without any requirement for animals or cells. Aptamer synthesis is far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These inherent characteristics of aptamers make them attractive for diagnostic applications.

A number of "molecular beacons" (often fluorescence compounds) can be attached to aptamers to provide a means for signaling the presence of and quantifying a target analyte. For instance, an aptamer specific for cocaine has recently been synthesized (Stojanovic, M. N. et al., "Aptamer-based folding fluorescent sensor for cocaine," *J. Am. Chem. Soc.*, 123(21):4928:31 (2001)). A fluorescence beacon, which quenches when cocaine is reversibly bound to the aptamer is used with a photodetector to quantify the concentration of cocaine present. Aptamer-based biosensors can be used repeatedly, in contrast to antibody-based tests that can be used only once.

Of particular interest as a beacon are amplifying fluorescent polymers (AFP). AFPs with a high specificity to TNT and DNT have been developed. Interestingly, a detector based on AFP technology also detects propofol, an intravenous anesthetic agent, in extremely low concentration. The combination of AFP and aptamer technologies holds the promise of robust, reusable biosensors that can detect compounds in minute concentrations with high specificity.

The term "biomarker" refers to a specific biochemical in the body that has a particular molecular feature to make it useful for diagnosing and measuring the progress of disease or the effects of treatment. For example, common metabolites or biomarkers found in a person's breath, and the respective diagnostic condition of the person providing such metabolite include, but are not limited to, acetaldehyde (source: ethanol, X-threonine; diagnosis: intoxication), acetone (source: acetoacetate; diagnosis: diet/diabetes), ammonia (source: deamination of amino acids; diagnosis: uremia and liver disease), CO (carbon monoxide) (source: $CH_2Cl_2$, elevated % COHb; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), and $Me_2S$ (source: infection; diagnosis: trench mouth).

Mechanisms of drug metabolism are extremely complex and are influenced by a number of factors including competitive binding on protein and red blood cells with other molecules, enzymatic activity, particularly in the liver, protein, and red blood cell concentration and a myriad of other factors. Exhaled breath holds the promise of a diagnostic technique, which can measure drug concentration real-time and thereby allow convenient determination of pharmacokinetics and pharmacodynamics of multiple compounds in real-time.

Accordingly, there are a number of medical conditions that can be monitored by detecting and/or measuring biomarkers present in a person's breath and other bodily fluids. While there has been technology generated towards the synthesis and use of aptamers and other multimolecular devices as biosensors, there exists little technology that address the use of exhaled breath in conjunction with apatmers as biosensors for the diagnosis and treatment of disease or as detectors for a wide range of naturally occurring and synthetic compounds. It is therefore desirable to provide a low-cost means for accurately and timely detecting and/or measuring the presence of metabolites in a person's bodily fluids in low concentrations via non-invasive methods. Further, in order to effectively apply exhaled breath sensing technology, there is a pressing need for an efficient screening method for determining which analytes/biomarkers are likely to be detectable in exhaled breath.

BRIEF SUMMARY

The present invention provides unique methods for detecting analytes/biomarkers of interest in bodily fluids. The invention utilizes aptamers, highly specific nucleic acid-based ligands, to non-invasively detect drugs, biomarkers, and other analytes in extremely low concentrations in exhaled breath and other bodily fluids. The invention includes aptamers attached to "molecular beacons" to provide a means for detecting and quantifying virtually any compound of interest in exhaled breath. The invention further includes aptamers in combination with nanotechnology (i.e., nanotubes) to provide an effective method for signaling the presence of a target analyte in bodily fluids, including but not limited to the blood.

In one embodiment, the present invention provides a method for analyzing analytes/biomarkers in exhaled breath using an aptamer attached directly to a volatile or "surrogate" biomarker. Volatile or "surrogate" biomarkers include substances and compounds that can be detected by various means. Volatile biomarkers become volatile after the aptamer attaches to the specific/target biomarker for which it was made. In a preferred embodiment, the volatile biomarker contains an amplifying fluorescent polymer (AFP).

In another embodiment, the present invention provides a method for analyzing analytes/biomarkers in bodily fluids, including blood, using a biosensor that includes a nanotube and an aptamer. The nanotube comprises a hollow tubular body defining an inner void, comprising a first end and a second end, and a volatile or "surrogate" biomarker contained within the hollow tubular body. In a preferred embodiment, the first end of the tubular body is open and a first end cap bound to an aptamer is positioned over the first open end to close the first end. The second end of the tube is closed or similarly capped as the first end.

According to the present invention, nanotubes containing volatile or "surrogate" biomarkers are provided that release the volatile or "surrogate" biomarkers from the nanotube under a variety of conditions to diagnose and/or treat a disease. In a preferred embodiment, an aptamer is designed for a biomarker of prostate cancer. Prostate cancers produce a protein, prostate specific antigen (PSA). An aptamer could be designed that is specific for PSA (PSA-aptamer). The PSA-aptamer can be attached to an end cap that fits on the end of a nanotube. A rapid test for the presence of prostate cancer, or a recurrence, could be developed where the volatile or "surrogate" biomarker is released from the nanotube after PSA (the biomarker of interest) interacts with the PSA-aptamer and "uncaps" the nanotubes. Using any of a number of previously disclosed detector technologies, the volatile biomarker is detected in exhaled breath, which indicates the presence of PSA in the blood.

Biosensing exhaled breath utilizing methods disclosed herein can be applied to a wide range of point of care (POC) diagnostic tests. For example, potential applications include detection of licit and illicit drugs, detection of a wide range of biomarkers related to specific diseases, and detection of any other compounds that appear in blood or other bodily fluids. These tests can be highly quantitative with the quantity of volatile or "surrogate" biomarker released/detectable being proportional to the quantity of a target compound in a sample of bodily fluid.

Moreover, exhaled breath detection using the method of the present invention can evaluate the efficacy of interventions in real-time. For example, it is known that isoprostane levels increase in cerebral spinal fluid and blood after traumatic brain injury. If isoprostane is readily detectable in exhaled breath by using an isoprostane specific biosensor according to the present invention, it can be possible to evaluate the efficacy of interventions in real-time for treating traumatic brain injury. In addition, the method of the present invention can also evaluate pharmacodynamics and pharmacokinetics for drug interventions in individuals.

The present invention also provides an effective and efficient method for screening analytes/biomarkers likely to be detectable in exhaled breath. Presently, it is unclear how often and to what extent disease specific biomarkers are present in exhaled breath. An embodiment of the present invention includes a screening process employing human blood placed in small vials to provide a cost-effective means to screen a wide variety of samples in conjunction with standard diagnostic equipment.

In a preferred embodiment, biomarkers detectable in exhaled breath are screened by the following steps: (1) providing samples of human blood free of potential biomarkers or including potential biomarkers, (2) incubating the blood samples at body temperature, and (3) measuring the concentration of a biomarker in whole blood, plasma, an ultrafiltrate, and/or in headspace. Preferably, a target biomarker is added to vials containing a small amount of blood in concentrations in the range likely to be found in vivo. The sample vials are incubated at body temperature and the concentration of the target biomarker in whole blood, plasma, in an ultrafiltrate, and in headspace are measured using conventional quantitative devices, such as LC-MS (liquid chromatography-mass spectroscopy) which is capable of measuring concentrations in parts per trillion. Free biomarkers/analytes (in ultrafiltrate) should be in equilibrium with biomarkers/analytes present in headspace. Target biomarkers present in headspace can be identified as those likely to be present in exhaled breath. The screening methodology according to the subject invention enables the production of a vast library of drugs, biomarkers, and other analytes likely to be present in bodily fluids.

In another embodiment, the screening method according to the present invention can include providing blood specimens from patients with known diseases (i.e., Alzheimer's disease, multiple sclerosis) and screening the specimens for the presence of biomarkers in blood components and exhaled breath.

DETAILED DISCLOSURE

The present invention provides a method for detecting biological conditions through noninvasive analysis of bodily fluid samples, including exhaled breath and blood. The present invention also includes methods for screening those analytes/biomarkers and their concentrations likely to be present in exhaled breath. A focus of the present invention is on the detection of analytes/biomarkers in an individual's bodily fluids indicative of conditions or diseases such as intoxication, cancer, renal failure, liver disease, or diabetes.

Definitions

Generally, according to the present invention, aptamers are utilized to detect whether there exist certain analytes/biomarkers within a subject fluid sample. The term "aptamer," as used herein, refers to an oligonucleotide chain that has a specific binding affinity for a target compound or molecule of interest. Aptamers include nucleic acids that are identified from a candidate mixture of nucleic acids.

The term "molecular beacon," as used herein, refers to a molecule or group of molecules (i.e., a nucleic acid molecule hybridized to an energy transfer complex or chromophore(s)) that can become detectable and can be attached to an aptamer under preselected conditions.

As used herein, "biomarkers" refer to naturally occurring or synthetic compounds, which are a marker of a disease state or of a normal or pathologic process that occurs in an organism (i.e., drug metabolism). The term "analyte," as used herein, refers to any substance, including chemical and biological agents such as nucleic acids, proteins, illicit drugs, explosives, toxins, pharmaceuticals, carcinogens, poisons, allergens, and infectious agents, that can be measured in an analytical procedure.

The term "volatile or 'surrogate' biomarker," as used herein, refers to a molecule or compound that is detectable by means of its physical or chemical properties as an indication that a target analyte/biomarker is present in a patient's body. Such volatile or "surrogate" biomarkers preferably include olfactory markers (odors) that are detectable in exhaled breath or by a number of sensor technologies including, for example, AFPs. Volatile or "surrogate" biomarkers can be detected using a method according to the subject invention or by devices and methods known in the art including, but not limited to, gas chromatography, electronic noses, spectrophotometers to detect the volatile biomarker's infrared (IF), ultraviolet (UV), or visible absorbance or fluorescence, or mass spectrometers to detect characteristic mass display of a "surrogate" biomarker.

Aptamer Technology

The present invention preferably utilizes aptamers to non-invasively detect drugs, biomarkers, and other analytes in exhaled breath and other bodily fluids, such as blood. In one embodiment, the invention includes aptamers attached to "molecular beacons" to provide a means for detecting and quantifying virtually any compound of interest in exhaled breath. In another embodiment, the invention includes aptamers in combination with nanotechnology (i.e., nanotubes) to provide an effective method for signaling the presence of a target analyte in bodily fluids, particularly in blood.

The discovery of the SELEX™ (Systematic Evolution of Ligands by EXponential enrichment) process enabled the identification of aptamers that recognize molecules other than nucleic acids with high affinity and specificity (Ellington and Szostak, "In vitro selection of RNA molecules that bind specific ligands," *Nature*, 346:818–822 (1990); Gold et al., "Diversity of oligonucleotide functions," *Ann. Rev. Biochem.*, 64:763–797 (1995); Tuerk and Gold, "Systematic evolution of ligands by exponential enrichment —RNA ligands to bacteriophage-T4 DNA-polymerase," *Science*, 249:505–510 (1990)). Aptamers have been selected to recognize a broad range of targets, including small organic molecules as well as large proteins (Gold et al., supra.; Osborne and Ellington, "Nucleic acid selection and the challenge of combinatorial chemistry," *Chem. Rev.*, 97:349–370 (1997)).

The aptamers derived from the SELEX process, as described in U.S. Pat. No. 5,475,096; U.S. Pat. No. 5,270,163; and WO 91/19813, may be utilized in the present invention. These patents describe a method for making aptamers, each having a unique sequence and the property of binding specifically to a desired target compound or molecule. The SELEX process is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. See also Jayasena, S., "Aptamers: An Emerging Class of Molecules That Rival Antibodies for Diagnostics," *Clinical Chemistry*, 45:9, 1628–1650 (1999).

Certain types of aptamer that can be used in the present invention include those described in U.S. Pat. No. 5,656,739 (hereinafter the '739 patent), which discloses the advantages of synthetic oligonucleotides as assembly templates. The '739 patent describes nucleic acids as particularly useful assembly templates because they can be selected to specifically bind nonoligonucleotide target molecules with high affinity (e.g., Tuerk and Gold (1990), supra), and because they can hybridize by complementary base pairing. Both forms of recognition can be programmably synthesized in a single molecule or hybridized into a single discrete structure.

Molecular Beacons

In an embodiment of the present invention, molecular beacons are attached to aptamers to provide a means for signaling and quantifying detected target analytes/biomarkers in exhaled breath. Molecular beacons, for example, employ fluorescence resonance energy transfer-based methods to provide fluorescence signals in the presence of a particular analyte/biomarker of interest (see Stojanovic, M. et al., "Aptamer-Based Folding Fluorescent Sensor for Cocaine," *J. Am. Chem. Soc.*, 123:4928–4931 (2001)). The aptamer acts as a sensor to detect the presence of a specific target analyte/biomarker. Upon detection of the analyte/biomarker, the aptamer communicates with a molecular beacon to generate a detectable signal.

Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission.

Molecular beacons and AFPs, including their methods for preparation, that can be used in the present invention are described in numerous patents and publications, including U.S. Pat. No. 6,261,783 and Fisher, M. et al., "A Man-Portable Chemical Sniffer Utilizing Novel Fluorescent Polymers for Detection of Ultra-Trace Concentrations of Explosives Emanating from Landmines," Paper from the 4th International Symposium on "Technology and the Mine Problem" held at the Naval Postgraduate School in Monterey, Calif., on Mar. 12–16, 2000, Nomadics, Inc.

Nanotechnology

Nanoparticle-based delivery systems offer the potential for controlled release of a signal upon detection of a target analyte/biomarker in bodily fluids. The present invention provides a unique method for diagnosing a condition and/or disease in a patient by utilizing a nanoparticle-based biosensor that includes nanoparticles, aptamers, and volatile or "surrogate" biomarkers. Nanoparticles are preferably in the form of tubular bodies ("nanotubes"). Nanotubes can be produced in a wide range of sizes and composed of a wide range of materials, or combination of materials, optimized for in-vivo delivery. Preferably, nanotubes intended for in-vivo use are of a length less than 500 nm and a diameter less than 200 nm. Because of concerns over occlusion of blood flow at the microvasculature level, it is important not to make nanoparticles too large for intravenous applications.

A number of patents and publications describe nanotube technology. For example, U.S. Pat. No. 5,482,601 to Ohshima et al. describes a method for producing carbon nanotubes. Other methods for making and using nanotubes include the non-carbon nanotubes of Zettl et al., U.S. Pat. No. 6,063,243, and the functionalized nanotubes of Fisher et al., U.S. Pat. No. 6,203,814.

According to the present invention, the nanotube is hollow and has two ends, preferably wherein a first end is open and a second end is closed. The first open nanotube end can be blocked with an end cap so as to prevent the release of the contents within the hollow interior of the nanotube. In a preferred embodiment, an aptamer is attached to the end cap to block the first open end of the nanotube.

Suitable end caps used to block a nanotube opening include, for example, nanoparticles having a diameter slightly larger than the inside diameter of the nanotube, so as to occlude the open end of the nanotube. End caps are any piece of matter and can be composed of materials that are chemically or physically similar (or dissimilar) to the nanotube. The end cap can be a particle that has a maximum dimension of less than 100 μm. In a preferred embodiment, the end cap is of a spherical or spheroidal form. However, end caps of other shapes, including ellipsoidal, cylindrical, and irregular, can also be used.

As described herein, nanotubes can be prepared to include functionalized end caps with aptamers. A variety of methods are available to functionalize an end cap, depending on the composition of the end cap. For example, an end cap can be functionalized using well-known chemical methods such as those employed for polylactide synthesis. Functional groups (i.e., aptamers) can be introduced to functionalized end caps by copolymerization. Monomers derived from an amino acid or lactic acid can be synthesized using standard methods and then used for random copolymerization with lactide. Such functionalized end caps can allow for the application of aptamers to the end cap.

Aptamers can be attached to proteins utilizing methods well known in the art (see Brody, E. N. and L. Gold, "Aptamers as therapeutic and diagnostic agents," *J Biotechnol,* 74(1):5–13 (2000) and Brody, E. N. et al., "The use of aptamers in large arrays for molecular diagnostics," *Mol Diagn,* 4(4):381–8 (1999)). For example, photo-cross-linkable aptamers allow for the covalent attachment of aptamers to proteins. Such aptamer-linked proteins can then be immobilized on a functionalized end cap of a nanotube. For example, aptamer-linked proteins can be attached covalently to a nanotube end cap, including attachment of the aptamer-linked protein by functionalization of the end cap surface. Alternatively, aptamer-linked proteins can be covalently attached to an end cap via linker molecules. Non-covalent linkage provides another method for introducing aptamer-linked proteins to an end cap. For example, an aptamer-linked protein may be attached to an end cap by absorption via hydrophibic binding or Van der Waals forces, hydrogen bonding, acid/base interactions, and electrostatic forces.

Aptamer-attached end caps, according to the present invention, are bound to the nanotube until the detection of a target analyte/biomarker by the aptamer. End caps can be attached to nanotubes using a variety of methods. Methods for attaching an end cap to a nanotube include, but are not limited to, using: electrostatic attraction, hydrogen bonding, acid and/or basic sites located on the end cap/nanotube, covalent bonds, and other chemical linkages.

A volatile or "surrogate" biomarker is preferably present within the hollow interior of a nanotube. Upon detection of a target analyte/biomarker by an aptamer attached to an end cap, the volatile or "surrogate" biomarker can be released with the uncapping of the nanotube. The volatile or "surrogate" biomarker can then be detected using a method according to the subject invention or by devices and methods known in the art including, but not limited to, gas chromatography, electronic noses, spectrophotometers to detect the volatile biomarker's infrared (IF), ultraviolet (UV), or visible absorbance or fluorescence, or mass spectrometers to detect characteristic mass display of a "surrogate" biomarker. Preferable "surrogate" biomarkers include olfactory markers (odors) that are detectable in exhaled breath.

According to the present invention, a nanotube is designed to release its volatile or "surrogate" biomarker in the presence of a target analyte/biomarker. This is achieved by linking an aptamer specific to the target analyte/biomarker to the end cap of a nanotube to provide an "uncapping mechanism." The uncapping mechanism is based upon the detection by the aptamer-end cap of surface markers on cell types (i.e., cancer cells), proteins in the blood (i.e., PSA for prostate cancer), or drugs in the body (i.e., illicit drugs or therapeutic drugs). The uncapping mechanism may require the use of energy-bearing biomolecular motors such as, but not limited to, the actin-based system (Dickinson, R. B. and D. L. Purich, "Clamped filament elongation model for actin-based motors," *Biophys J.,* 82:605–617 (2002)).

Nanoparticle-based biosensors, according to the present invention, can be administered utilizing methods known to the skilled artisan. For example, nanoparticle-based biosensors can be administered intravenously, intradermally, subcutaneously, orally or nasally (i.e., inhalation), transdermally (i.e., topical), transmucosally, and via the rectum.

Nanoparticle-based sensors for use in an organism can be prepared from biodegradable polymers and/or biocompatible polymers. As used herein, a "biodegradable" substance refers to a substance that can be decomposed by biological agents or by natural activity within an organism. Examples of contemplated biodegradable polymers include, but are not limited to: polyesters such as poly(caprolactone), poly(glycolic acid), poly(lactic acid), and polyhydroxybutrate; polyanhydrides such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

As used herein, a "biocompatible" substance includes those substances that are compatible with and have demonstrated no significant toxic effects on living organisms. Examples of contemplated biocompatible polymers include PLG (Poly(lactide-co-glycolide)), poly(ethylene glycol), and copolymers of poly(ethylene oxide) with poly(L-Lactic acid) or with poly(β-benzyl-L-aspartate). In a preferred embodiment, biocompatibility includes immunogenic compatability. An immunogenically compatible substance can include a substance that, when introduced into a body, does not significantly elicit humoral or cell-based immunity.

Further, a number of approaches can be used to make the surface of a nanoparticle-based biosensor according to the present invention both biocompatible and "stealthy." For example, this can be accomplished by attaching a PEG-maleimide to the chain-end thiols on the outer surfaces of a nanoparticle. If the nanoparticle is in the shape of a tube and composed of gold or similar metals, the PEG chain can be attached by a thiol linker as described in Yu, S. et al., "Size-Based Protein Separations in Poly(ethylene glycol)-Derivatized Gold Nanotubule Membranes," *Nano Letters*, 1, 495–498 (2001). Other examples of biocompatible polymers and surface treatments can be found in Majeti N. V. Ravi Kumar, "Nano and Microparticles as Controlled Drug Delivery Devices," *J. Pharm. Pharmaceut. Sci.*, 3(2):234–258 (2000).

The present invention provides methods for assessing the efficacy of interventions in real-time. For example, it is known that isoprostane levels increase in cerebral spinal fluid and blood after traumatic brain injury. Isoprostane may be readily detectable in exhaled breath. In accordance with the present invention, an aptamer-biosensor can be used to detect and measure isoprostane levels in patients who have suffered traumatic brain injury. By measuring isoprostane levels, a clinician can follow the course of the brain injury. In addition, a nanoparticle-based aptamer-biosensor can be incorporated into pharmaceutical compositions to treat traumatic brain injury. Moreover, by presenting an isoprostane specific aptamer-biosensor to exhaled breath in accordance with the present invention, it can be possible to evaluate the efficacy of interventions in real-time for treating traumatic brain injury. Accordingly, the method of the present invention can also evaluate pharmacodynamics and pharmacokinetics for drug interventions in individuals.

In an embodiment, a nanotube according to the present invention can detect the appearance of cancer antigens on the walls of cancer cells, cause uncapping which in turn releases a volatile or "surrogate" biomarker that can be readily detected in the breath, and thereby notify the patient or his/her physician that a cancer cell (s) was encountered in the patient's body.

Exemplary Method for Diagnosing Bronchogenic Carcinoma

In a preferred embodiment, an aptamer is designed for a biomarker of bronchogenic carcinoma. Bronchogenic carcinomas produce carcinoma metabolites that cause the occurrence of O-toluidine in exhaled breath. An aptamer can be designed using routine techniques that is specific for O-toluidine (O-toluidine-aptamer). The O-toluidine-aptamer can be linked with a molecular beacon, such as an AFP, to form an OT-biosensor. Upon exposing an OT-biosensor to exhaled breath suspected of containing O-toluidine, the O-toluidine-aptamer specifically binds to any O-toluidine present and causes the molecular beacon, such as AFP, to generate a signal. Thus, a time- and cost-efficient test for the presence of bronchogenic carcinoma is provided.

Exemplary Method for Diagnosing Prostate Cancer

In another preferred embodiment, an aptamer is designed for a biomarker of a specific cancer, i.e., prostate cancer. Prostate cancers produce a protein, prostate specific antigen (PSA). An aptamer can be designed, using routine techniques, that is specific for PSA (PSA-aptamer). The PSA-aptamer can be attached to an end cap that fits on the end of a nanotube. In a rapid test for the presence of prostate cancer, or a recurrence, the volatile or "surrogate" biomarker is released from the nanotube after PSA (the biomarker of interest) interacts with the PSA-aptamer and "uncaps" the nanotubes. Using any of a number of previously disclosed detector technologies, the volatile biomarker is detected in exhaled breath that indicates the presence of PSA in the blood.

Screening Method According to the Present Invention

The present invention provides methods for determining which analytes/biomarkers and their concentrations are likely to be detectable in exhaled breath. Human blood is preferably employed. In one embodiment, human blood free of potential target analytes/biomarkers is screened as a baseline/control. In another embodiment, target analytes/biomarkers are added to human blood that is subsequently screened. The target analytes/biomarkers are preferably added to human blood in concentrations likely to be found in vivo in blood. The human blood (with or without target analytes/biomarkers) is then placed in closed containers and incubated at body temperature.

After incubation, the concentration of the target analyte/compound is assessed in whole blood, plasma, in an ultrafiltrate, and in the headspace using conventional quantitative/analytic devices including, but not limited to, liquid chromatography-mass spectroscopy (LS-MS) or gas chromatography-mass spectroscopy (GC-MS). Theoretically, the amount of target analyte/biomarker present in the ultrafiltrate should be proportional to the concentration detectable in exhaled breath. Measuring the amount of target analyte/biomarker in the headspace can provide a more accurate assessment of target analyte/biomarker concentration in exhaled breath. In a preferred embodiment, human blood samples including known target analytes/biomarkers are placed in vials and incubated at 98° F. The concentration of the target analyte/biomarker likely to be present in exhaled breath is assessed by measuring the amount of target analyte/biomarker present in the headspace using GC-MS.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for detecting a target analyte/biomarker in exhaled breath comprising:
   a.) exposing to the exhaled breath an aptamer that selectively binds to the target analyte/biomarker, wherein the aptamer is linked with a molecular beacon; and
   b.) detecting a signal generated by the molecular beacon to indicate the presence of the target analyte/biomarker in the exhaled breath,
   wherein the target analyte/biomarker is selected from the group consisting of acetaldehyde, acetone, ammonia, CO, chloroform, dichlorobenzene, diethylamine, hydrogen, isoprene, isoprostane, methanethiol, methylethylketone, O-toluidine, pentane sulfides and sulfides, $H_2S$, MES, and $Me_2S$.

2. The method according to claim 1, wherein the molecular beacon is an amplifying fluorescent polymer.

* * * * *